United States Patent
Jakob et al.

(10) Patent No.: US 10,422,778 B2
(45) Date of Patent: Sep. 24, 2019

(54) METHOD FOR DETERMINING DIMETHYL DISULPHIDE

(71) Applicant: Evonik Degussa GmbH, Essen (DE)

(72) Inventors: Harald Jakob, Hasselroth (DE); Benjamin Fonfe, Frankfurt (DE); Sebastian Fuss, Flieden (DE); Andreas Doerflein, Grosskrotzenburg (DE); Markus Held, Limeshain (DE); Nadine Duerr, Alsbach (DE)

(73) Assignee: Evonik Degussa GmbH, Essen (DE)

( * ) Notice: Subject to any disclaimer, the term of this patent is extended or adjusted under 35 U.S.C. 154(b) by 112 days.

(21) Appl. No.: 15/537,592

(22) PCT Filed: Dec. 17, 2015

(86) PCT No.: PCT/EP2015/080167
§ 371 (c)(1),
(2) Date: Jun. 19, 2017

(87) PCT Pub. No.: WO2016/097109
PCT Pub. Date: Jun. 23, 2016

(65) Prior Publication Data
US 2018/0267002 A1 Sep. 20, 2018

(30) Foreign Application Priority Data
Dec. 19, 2014 (EP) .................................. 14199254

(51) Int. Cl.
*G01N 27/49* (2006.01)
*G01N 30/88* (2006.01)
*G01N 30/64* (2006.01)

(52) U.S. Cl.
CPC ............. *G01N 30/88* (2013.01); *G01N 27/49* (2013.01); *G01N 2030/645* (2013.01); *G01N 2030/884* (2013.01)

(58) Field of Classification Search
CPC .. G01N 30/88; G01N 27/49; G01N 2030/884; G01N 2030/645
See application file for complete search history.

(56) References Cited

U.S. PATENT DOCUMENTS

| 2014/0357897 A1 | 12/2014 | Fonfe et al. |
| 2015/0308720 A1 | 10/2015 | Zehnacker et al. |
| 2016/0176808 A1 | 6/2016 | Fonfe et al. |

(Continued)

FOREIGN PATENT DOCUMENTS

WO    WO 2012/052755 A1    4/2012

OTHER PUBLICATIONS

Meinardi et al., "Dimethyl disulfide (DMDS) and dimethyl sulfide (DMS) emissions from biomass burning in Australia", 2003, Geophysical Research Letters, vol. 30, No. 9, 1454, pp. 1-4 (Year: 2003).*

(Continued)

*Primary Examiner* — David Z Huang
(74) *Attorney, Agent, or Firm* — Oblon, McClelland, Maier & Neustadt, L.L.P.

(57) ABSTRACT

A method for determining dimethyl disulphide proceeds by carrying out a chromatographic separation of an analyte containing at least dimethyl disulphide and methanesulphonic acid, and determining the dimethyl disulphide by pulsed amperometric detection.

14 Claims, 9 Drawing Sheets

Chromatogram of comparative example 1

(56) References Cited

U.S. PATENT DOCUMENTS

2016/0304446 A1 10/2016 Fonfe et al.
2018/0133704 A1 5/2018 He et al.

OTHER PUBLICATIONS

Napier et al., "Voltammetric and Amperometric Studies of Selected Thiols and Dimethyldisulfide Using a Screen-Printed Carbon Electrode Modified with Cobalt Phthalocyanine: Studies Towards a Gas Sensor", May 3, 1996, Electroanalysis, 8, No. 11, pp. 1006-1013 (Year: 1996).*
U.S. Appl. No. 15/778,802, filed May 24, 2018, Fonfe et al.
U.S. Appl. No. 15/868,396, filed Feb. 23, 2018, Zehnacker et al.
International Search Report and Written Opinion of the International Searching Authority dated Apr. 13, 2016 in PCT/EP2015/080167 filed Dec. 17, 2015.
Somayeh Rajabzadeh, et al., "Development of a Dimethyl Disulfide Electrochemical Sensor Based on Electrodeposited Reduced Graphene Oxide-Chitosan Modified Glassy Carbon Electrode" Electrochimica Acta, vol. 135, XP028860075, May 21, 2014, pp. 543-549.
Igor Volov, et al., "Chromatography of Bis-(3-Sulfopropyl) Disulfide and its Breakdown Products by HPLC Coupled with Electrochemical Detection" Journal of Separation Science, vol. 34, No. 18, XP055195080, Aug. 2, 2011, pp. 2385-2390.
Dennis C. Johnson, et al., "Pulsed Amperometric Detection of Carbohydrates, Amines and Sulfur Species in Ion Chromatography—the Current State of Research", Journal of Chromatography, vol. 640, No. 1-2, XP026570933, Jun. 25, 1993, pp. 79-96.
William R. LaCourse, et al., "Pulsed Electrochemical Detection of Thiocompounds Following Microchromatographic Separations" Analytica Chimica Acta, vol. 307, No. 2-3, XP005259734, May 30, 1995, pp. 301-319.
Diana Maria Serafim, et al., "Determination of Sulfur Compounds in Gasoline Using Mercury Film Electrode by Square Wave Voltammetry" vol. 87, No. 7, XP022495836, Feb. 22, 2008, pp. 1007-1013.

* cited by examiner

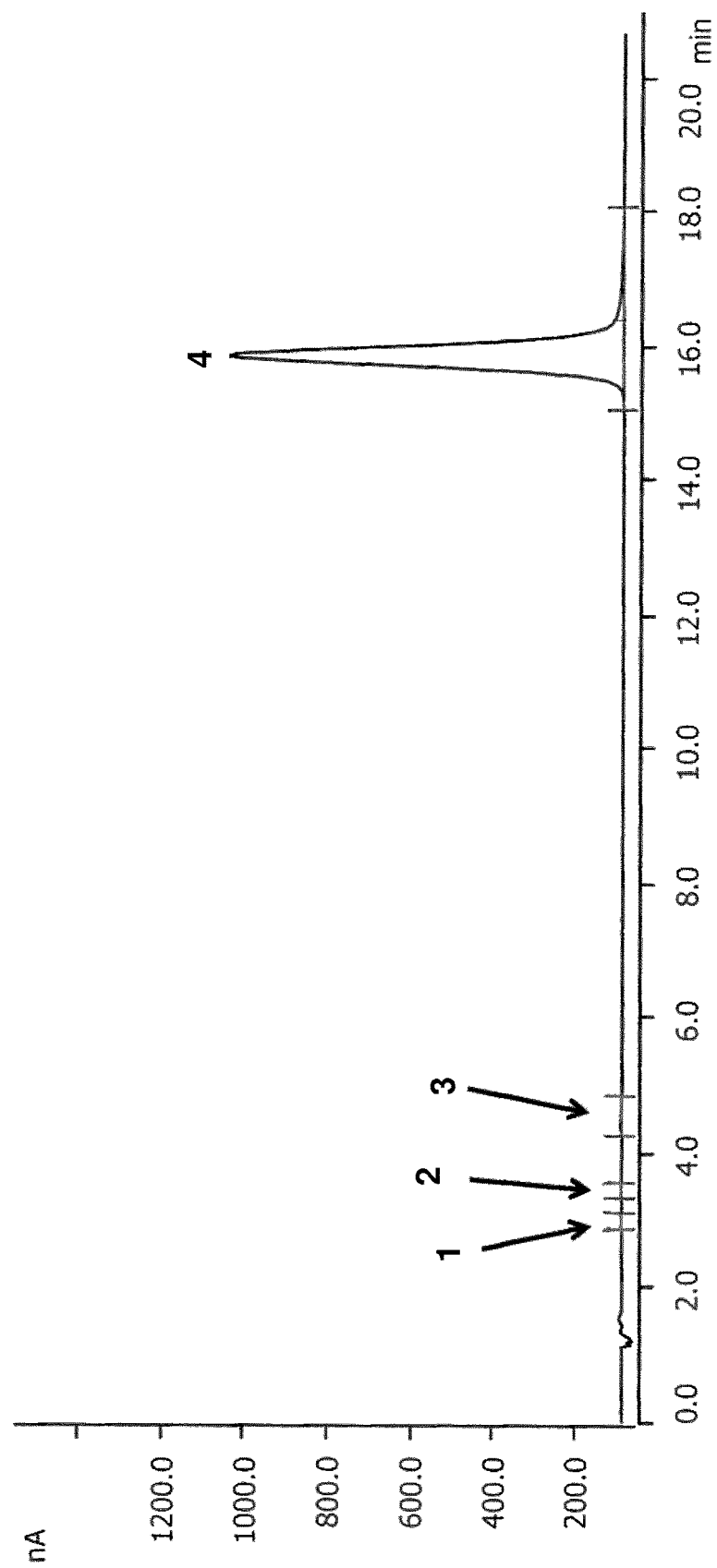
Fig. 1  Chromatogram of comparative example 1

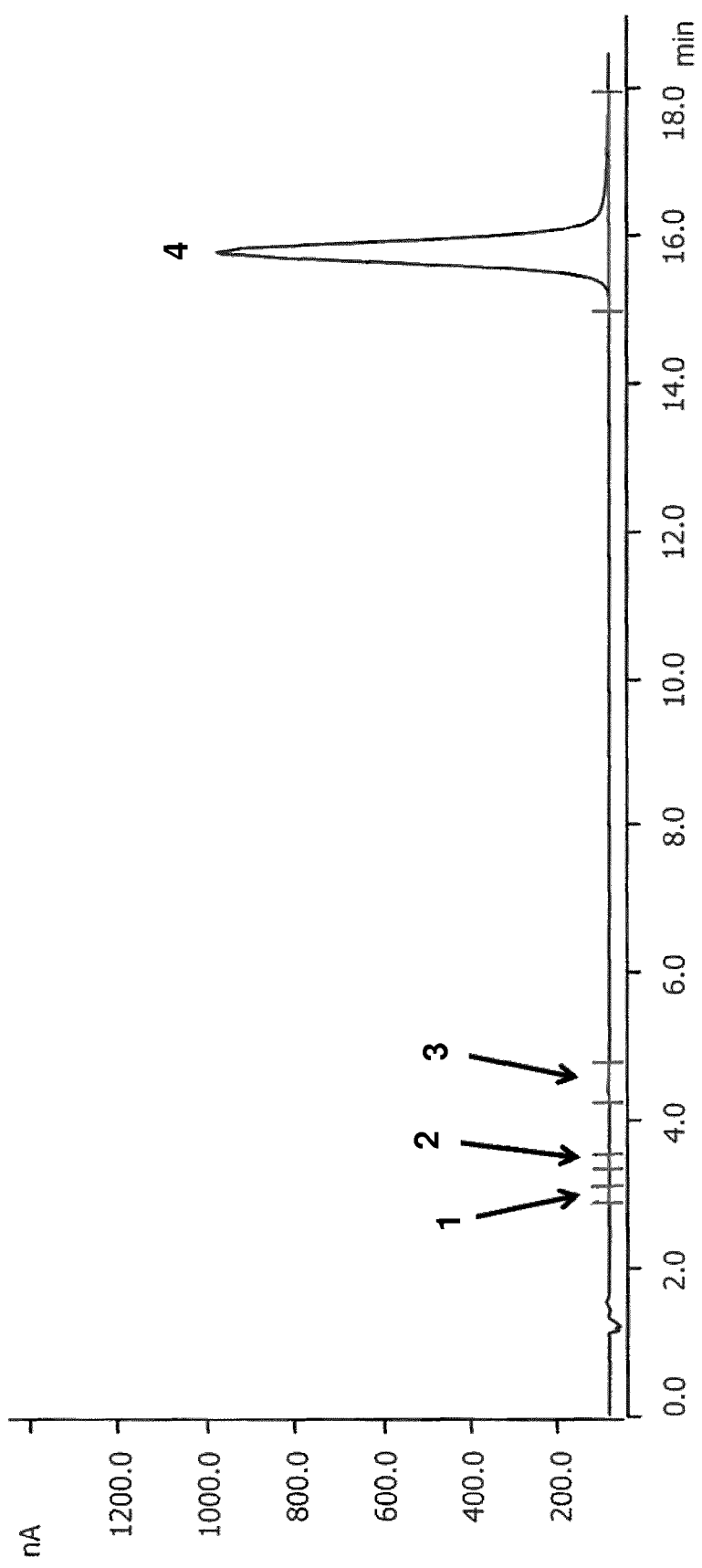
Fig. 2  Chromatogram of comparative example 2

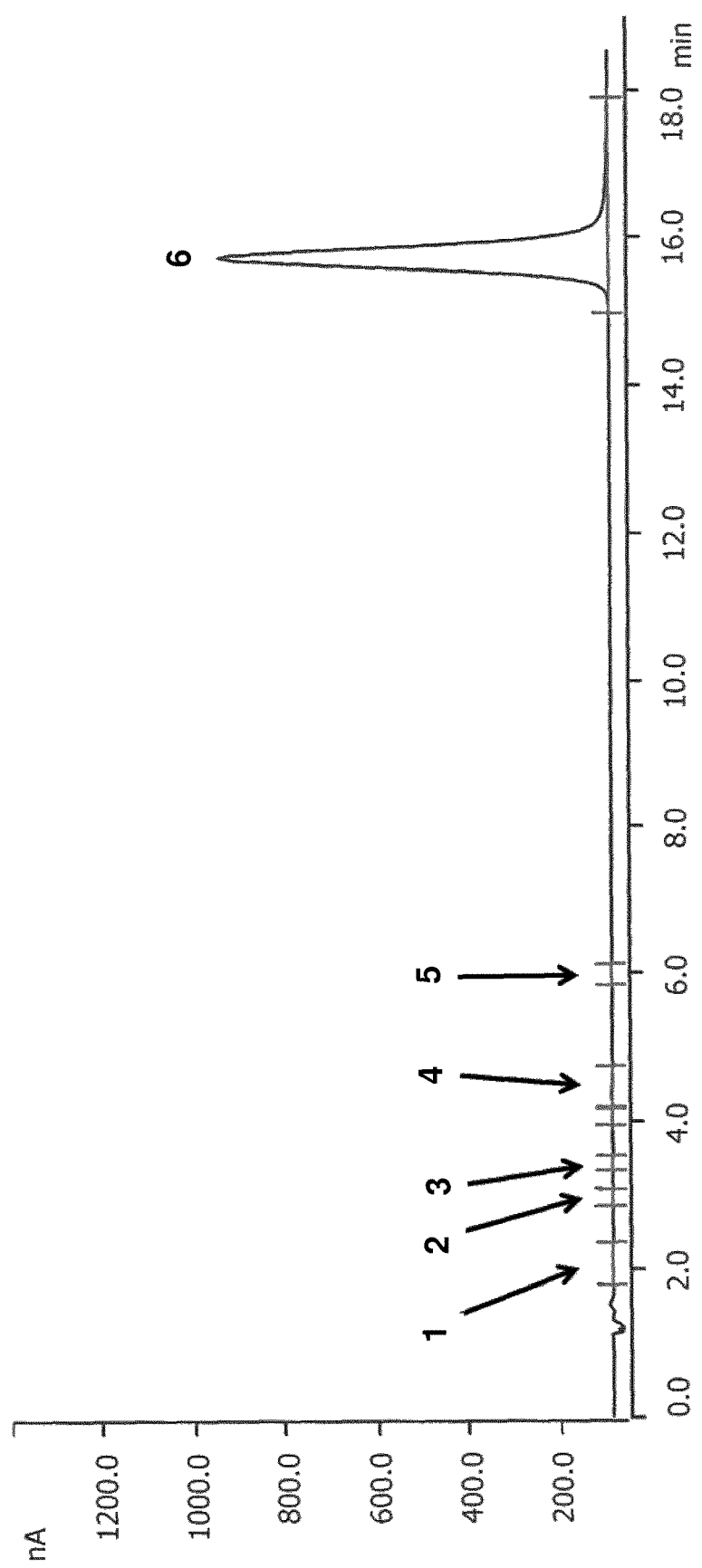
Fig. 3 Chromatogram of comparative example 3

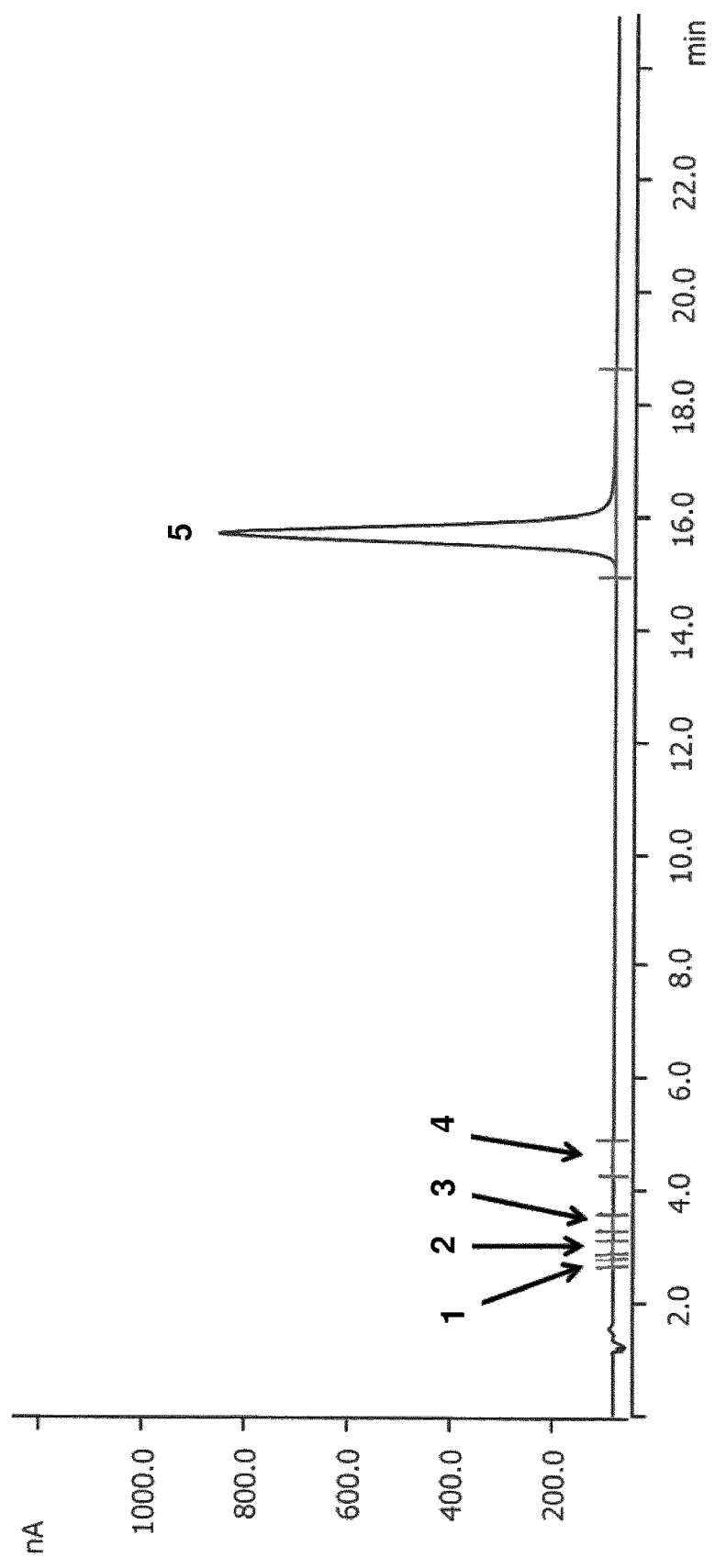

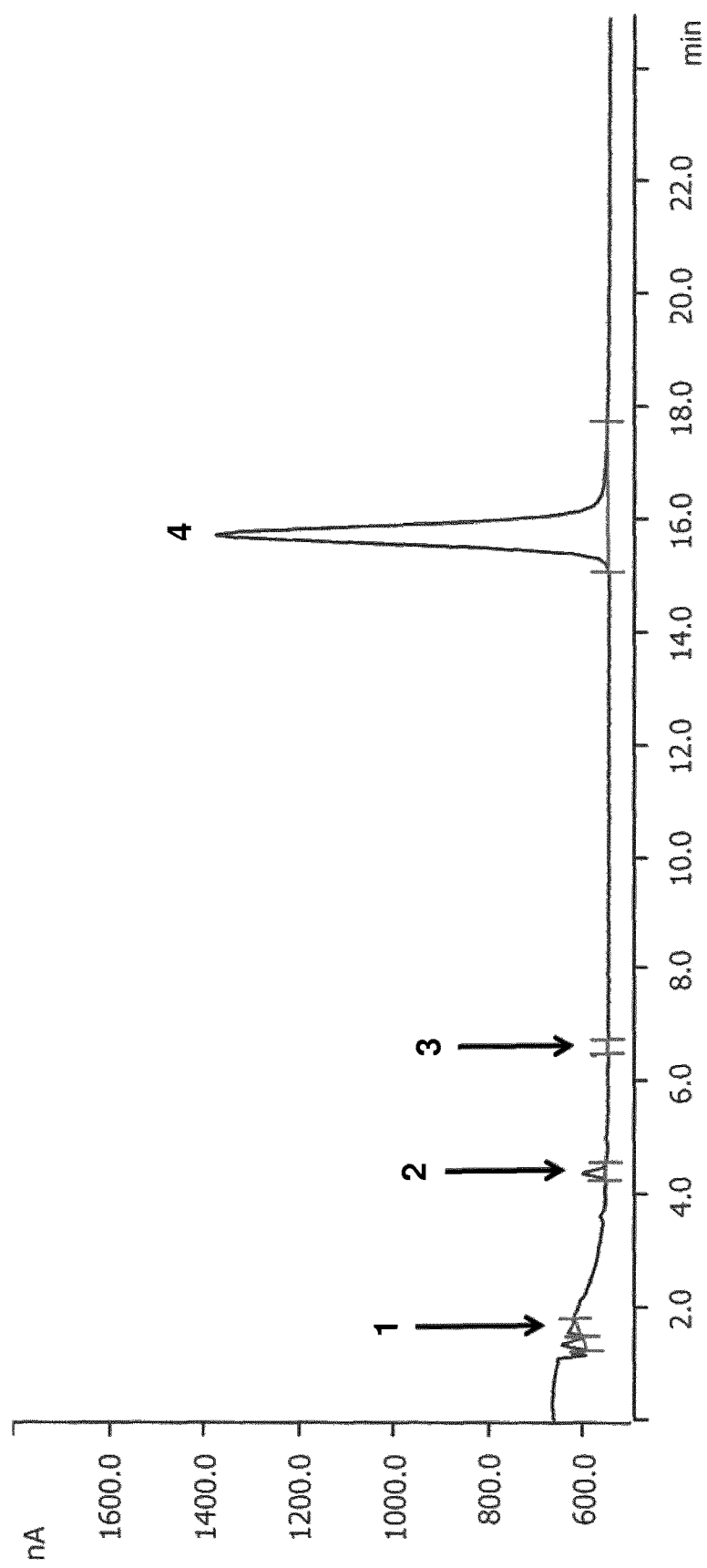
Fig. 5   Chromatogram of example 1

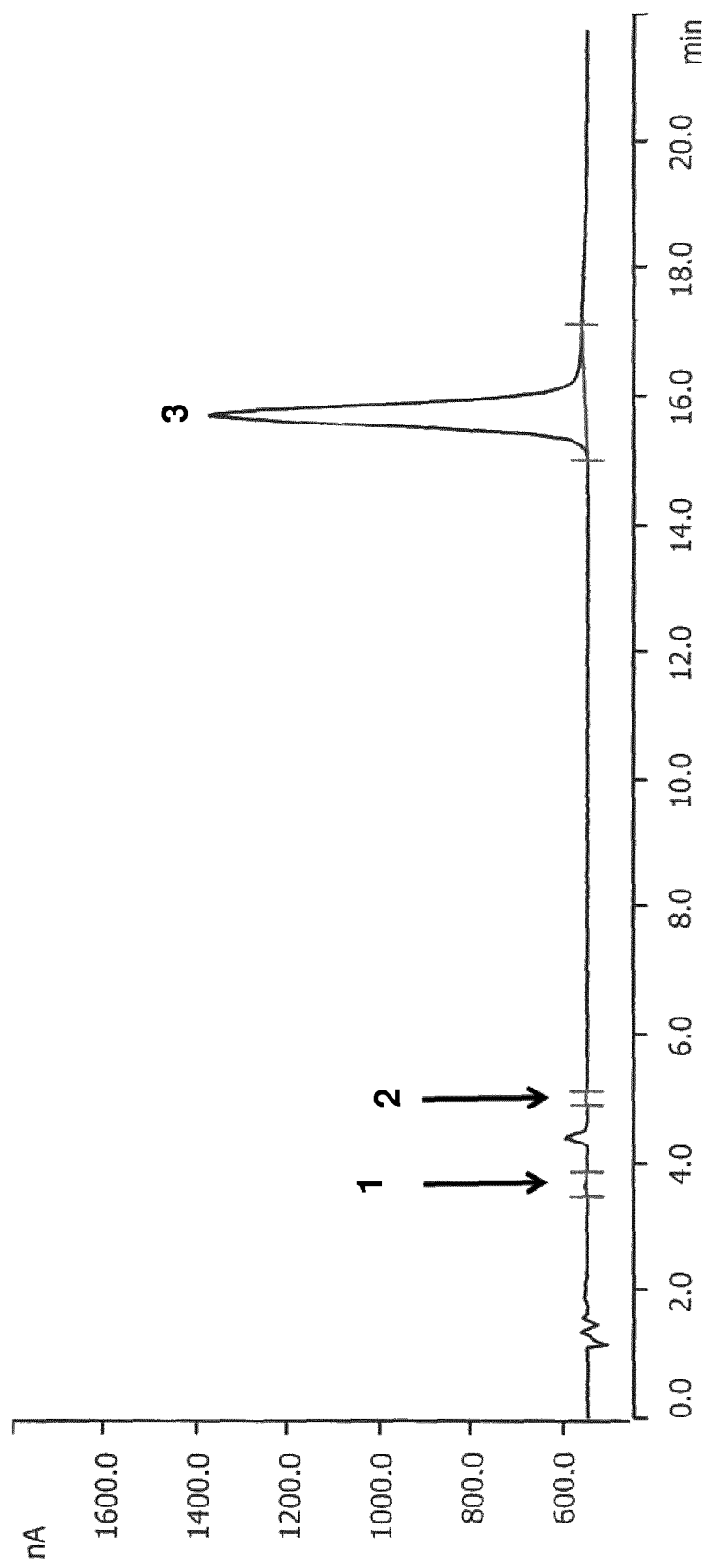
Fig. 6  Chromatogram of example 2

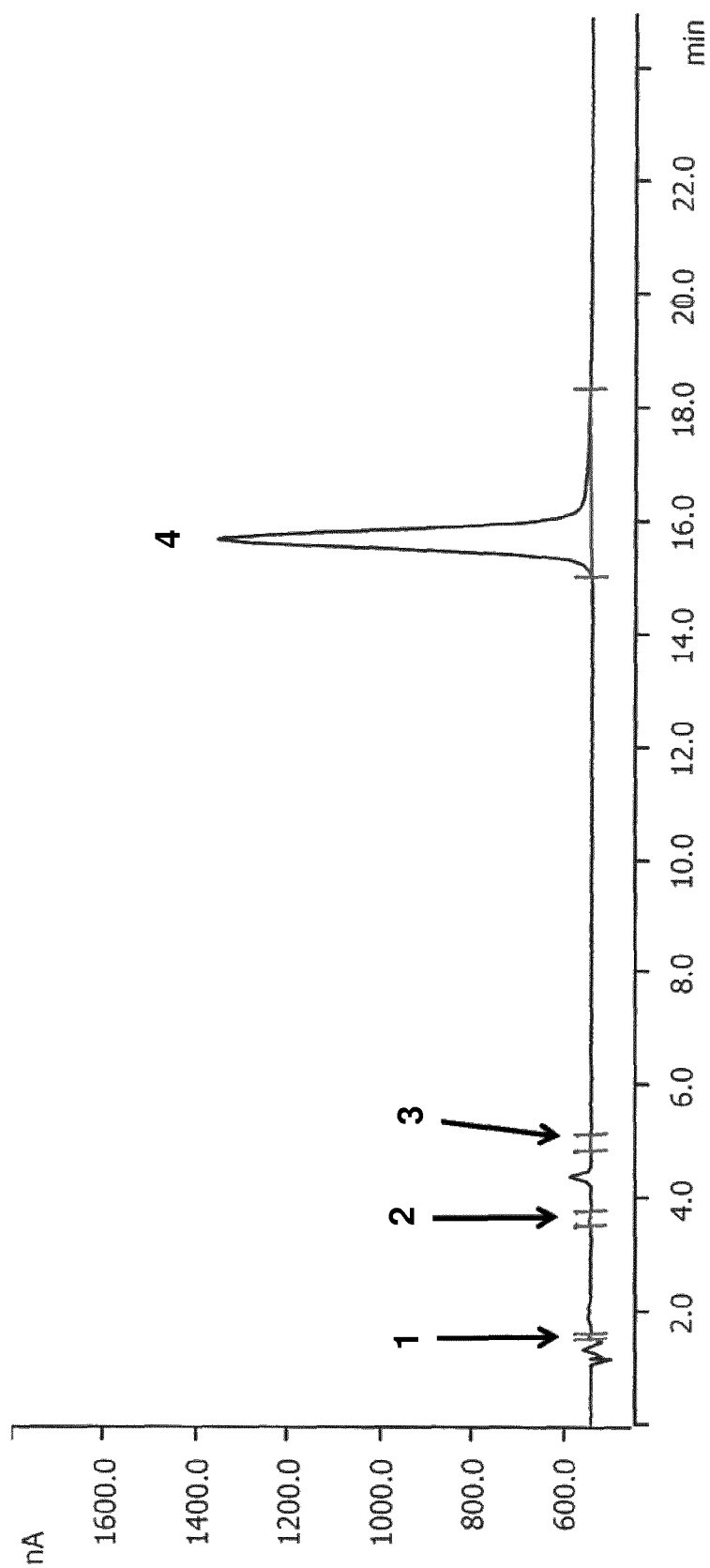
Fig. 7 Chromatogram of example 3

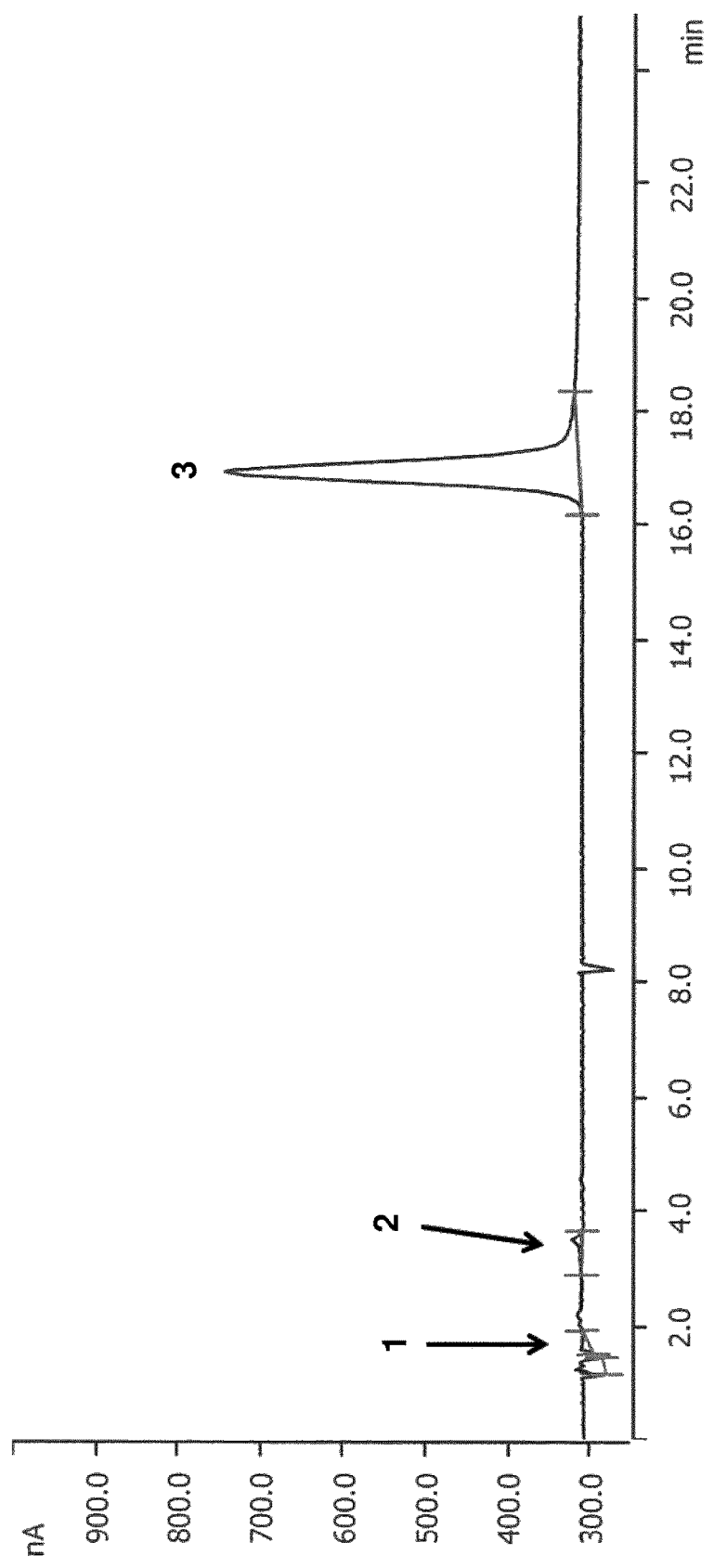
Fig. 8  Chromatogram of example 4

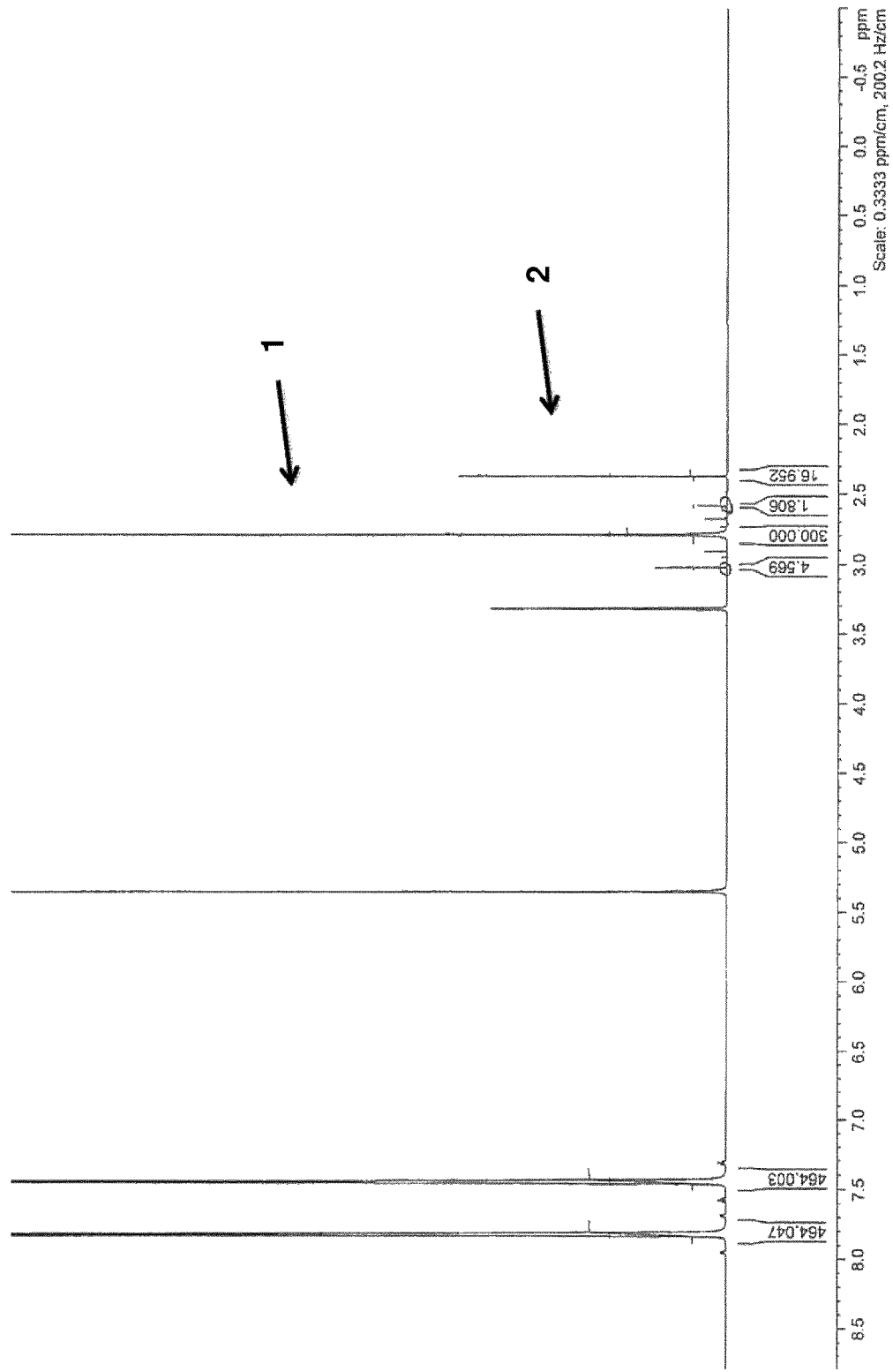
Fig. 9 NMR spectrum of comparative experiment 5

METHOD FOR DETERMINING DIMETHYL DISULPHIDE

The present invention relates to a method for determining dimethyl disulphide in a solution comprising methanesulphonic acid.

Dialkyl disulphides, sometimes referred to as disulphanes, are organic covalent disulphides of general formula $R^1$—S—S—$R^2$, where $R^1$ and $R^2$ are each an alkyl residue. In so-called symmetrical disulphides, $R^1$ and $R^2$ are identical, whereas in so-called asymmetrical disulphides the organic residue $R^1$ is different from the other residue $R^2$. The simplest representative of this substance class is dimethyl disulphide $H_3C$—S—S—$CH_3$, which may be prepared by reaction of methanethiol with elemental sulphur. Use of dimethyl disulphide includes as sulphiding agent in oil refineries and as auxiliary in the cracking of crude oil in the petrochemical industry. Dialkyl disulphides in general and dimethyl disulphide in particular are also increasingly important for the preparation of alkanesulponic acids, particularly methanesulphonic acid.

Alkanesulphonic acids are organic derivatives of sulphuric acid from which they differ structurally by the replacement of a hydroxyl group by an organic residue. The general structural formula of alkanesulphonic acids is therefore R—$SO_3$—H, where R refers to an organic residue, for example alkyl or aryl. Depending on this organic residue, aliphatic, aromatic or heterocyclic sulphonic acids are differentiated. The free sulphonic acids are generally colourless and hygroscopic substances whose acid strength corresponds to that of the inorganic acids. With a pKa of −5.5, trifluoromethanesulphonic acid is actually one of the strongest known acids and therefore belongs to the group of so-called superacids. In contrast to the sulphate salts of mercury, lead and silver, the corresponding sulphonates are very readily water-soluble.

The simplest representative of the alkanesulphonic acids is methanesulphonic acid, usually abbreviated also to MSA. At the same time, methanesulphonic acid is also the most economically important alkanesulphonic acid due to its numerous possible uses. For instance, methanesulphonic acid serves as solvent and catalyst for various organic reactions such as alkylations, esterifications, polymerizations or heterocyclic syntheses. Another field of application is the formation of acid addition salts of basic medicaments with methanesulphonic acid in human medicine. In addition, methanesulphonic acid is increasingly used as a constituent of detergents since it can be readily integrated into detergent solutions owing to its lack of colour and odour. Most important from an industrial point of view are the metal salts of methanesulphonic acid which are used as electrolytes in methanesulphonic acid galvanizing baths, particularly for preparing circuit boards for the electronics industry. A further novel field of application for methanesulphonic acid is so-called oil drilling: The strata conveying crude oil tapped by boreholes frequently does not liberate the oil or only in limited amounts. To improve liberation of the oil, therefore, the rock strata containing the oil are softened with methanesulphonic acid.

Alkanesulphonic acids are obtainable by oxidation of mercaptans and/or dialkyl disulphides or polysulphides. Methods for preparing alkanesulphonic acids are known from the published patent applications WO 98/34914 A1, WO 00/31027 A1 and CN 101648892 A and the U.S. Pat. Nos. 2,433,395, 2,433,396, 2,502,618, 2,498,318, 2,505,910, 2,697,722, 2,727,920. On an industrial scale, the preparation of alkanesulphonic acids from dialkyl disulphides is generally preferred.

To determine the process parameters which allow as far as possible a complete conversion of the dialkyl disulphide to the corresponding alkanesulphonic acid, a reliable determination of the dialkyl disulphide is therefore required. A method of determination suitable for this purpose should also allow as precise a determination as possible when the alkanesulphonic acid is present in excess compared to the dialkyl disulphide. This is typically the case when the alkanesulphonic acid, which is the oxidation product of the dialkyl disulphide, is also used as solvent for this reaction, as described in PCT/CN2013/089136.

For this application, however, the known analysis methods have proven to be either unsuitable or at least not sufficiently suitable. For example, using NMR analysis (nuclear magnetic resonance)—independent of the substance to be determined and the matrix concerned—detection limits of only approx. 0.1% by weight are achievable. However, this detection limit is too high for the application of determining dialkyl disulphides in alkanesulphonic acids. A further disadvantage of nuclear magnetic resonance is that NMR spectrometers are highly sophisticated, cost-intensive and maintenance-intensive analytical instruments whose use directly in the vicinity of a production plant is impractical. NIR analysis (near infrared spectroscopy) is subject to the same limitations relating to the detection limit. An additional disadvantage of this method is that it also requires a sufficiently precise validation method for the calibration. UV spectroscopy (ultraviolet) also does not provide satisfactory results for the application underlying the present invention. For example, the use of a high performance liquid chromatograph (HPLC) with a UV detector allows the determination of dimethyl disulphide only within an error of about 10% at 1% by weight dimethyl disulphide. Analysis by means of so-called headspace gas chromatography (GC, gas chromatography), in which only the vapour space above the sample is analysed, whereby the analyte has hardly any influence, is not suitable for the present application. This is because this method allows good results only in synthetic samples but leads only to unsatisfactory results in the determination of dialkyl disulphides in a real sample matrix.

No improvements are achieved by changing from high performance liquid chromatography to ion chromatography (IC, ion chromatography), since dialkyl disulphides such as dimethyl disulphide cannot be determined with the required precision using a UV detector. This also applies to the use of a conductivity detector and a refractive index detector for determining dimethyl disulphide.

A need therefore existed for a method for determining dimethyl disulphide in methanesulphonic acid with a lower detection limit.

According to the invention this object is achieved by combining a chromatographic separation method with pulsed amperometric detection.

The present invention therefore relates to a method for determining dimethyl disulphide comprising the steps of
a) carrying out a chromatographic separation of an analyte comprising at least dimethyl disulphide and methanesulphonic acid, and
b) determining the dimethyl disulphide by means of pulsed amperometric detection.

In order to be able to reliably determine the dialkyl disulphide, the analyte with the dialkyl disulphide to be determined must be subjected to processing. This is carried out in the context of the present invention by a chromatographic separation in which the analyte to be investigated together with an eluent, the so-called mobile phase, is passed through a so-called separating column comprising the stationary phase.

The dialkyl disulphide eluted from the separating column is detected with the aid of so-called pulsed amperometric detection. Amperometric detection or amperometry is an electrochemical method for the quantitative determination of chemical compounds. A basic prerequisite for the applicability of amperometry is that the chemical compounds to be determined are readily oxidizable or reducible substances. The setup of the detector cell in which the measurement takes place is based on a so-called potentiostatic measurement arrangement, and therefore has three electrodes in an appropriate detector cell: a working electrode which serves to monitor the electrochemical processes, an auxiliary electrode which transports the current from the oxidation or reduction, and a reference electrode which is switched at high impedance and therefore provides a uniform voltage at the working electrode; the current flow between working and auxiliary electrode is therefore measured. If the required potential for an oxidation or reduction of the organic compound in question is present at the working electrode, a signal current is measured as a consequence of this electrochemical reaction. The measured electrolysis current is subsequently enhanced and depicted as a function of time in a chromatogram. Since the electrolysis current is directly proportional to the concentration of the unreacted organic compounds in the electrolysis reaction, the amperometric detection allows the determination of unknown concentrations of a specific organic compound with the aid of a previously generated calibration function. In the context of the present invention, amperometric detection, in which only the potential required for carrying out the electrolysis reaction of the organic compound is applied at the working electrode, is referred to as amperometric detection at constant potential.

The object relating to the present invention has shown, however, that amperometric determination at constant potential still does not allow reproducible results for determining a dialkyl disulphide in an alkanesulphonic acid: the value determined on repeating a previous measurement for the electrolysis current is generally significantly lower than for the first measurement, for example, the measured value can decrease by more than 20% over a period of one hour. This is due firstly to the (partial) coverage of the working electrode with at least one absorbate and to the occurrence of capacitive currents. The at least one adsorbate may be a product of the electrochemical reaction which has taken place at the working electrode. The occurrence of capacitive currents is probably caused by the formation of a diffusion layer at the working electrode or diffusion thereof into the solution is hindered, which is due to the redistribution of electroactive species in the detector cell due to typical convection processes.

Precision and reproducibility of the amperometric detection are thereby achieved in accordance with the invention by pulsing. In the context of the present invention, so-called pulsed amperometric detection is understood to mean an amperometric detection in which the voltage applied to the working electrode for carrying out the electrolysis is overlaid at periodic time intervals by at least one rectangular pulse. This rectangular pulse can be either an anodic or cathodic potential or also a mixture of the two. By means of this technique, the working electrode is not only cleaned of the adsorbates adhering to its surface, but it is also conditioned for the next determinations. This conditioning improves the formation of the diffusion layer at the working electrode or diffusion thereof into the solution which likewise contributes to a considerable improvement in the precision and reproducibility of the pulsed amperometric detection compared to a "simple" amperometric detection at constant voltage.

The electrolysis current typically measured in a pulsed amperometric detection is not equal for all dialkyl disulphides, but depends on its structural composition in addition to the concentration of the relevant dialkyl disulphide. Prior to the determination of an unknown amount of a particular dialkyl disulphide, the electrolysis current is firstly therefore typically measured for solutions of different concentrations of the same, i.e. of the dialkyl disulphide to be determined. A calibration function is generated from these measured values in which the electrolysis current measured is correlated with the concentration of the dialkyl disulphide. Subsequently, the electrolysis current is measured for a sample with an unknown concentration of the dialkyl disulphide, for which a corresponding calibration function has been generated, by means of pulsed amperometric detection. The concentration of this dialkyl disulphide in the sample in question can be determined by comparing the measured electrolysis current with this calibration function generated for a specific dialkyl disulphide.

In one embodiment of the method according to the invention, the step to determine the dimethyl disulphide by means of pulsed amperometric detection therefore comprises the individual steps b1) measuring the electrolysis current for the dimethyl disulphide by means of pulsed amperometric detection, and b2) determining the amount and/or the concentration of the dimethyl disulphide to be determined by comparison with a calibration function previously generated for the dimethyl disulphide to be determined.

A necessary criterion to allow determination of an organic compound containing sulphur, such as a dialkyl disulphide, with the aid of amperometric detection, is the presence of at least one free electron pair on the sulphur atom. This is because only compounds having a free electron pair can be adsorbed on electrode surfaces and are therefore electroactive species. In contrast, organic compounds lacking free electron pairs are not electroactive species. This is because these compounds cannot be adsorbed on electrode surfaces due to the lack of electron pairs and therefore also cannot be determined by means of amperometric detection.

In a further embodiment of the method according to the invention, the pulsed amperometric detection is therefore carried out in oxidative mode.

Carrying out the pulsed amperometric detection in oxidative mode for determining dialkyl disulphide has the advantage that the relevant dialkyl disulphide adsorbed on the electrode surface is oxidized to compounds which are not electroactive. These oxidized species are therefore also not adsorbed on the electrode surface and do not directly influence the measurement in progress or subsequent measurements. This contributes to the precision of the method according to the invention. Therefore, in the context of the present invention, a pulsed amperometric detection in oxidative mode is in principle understood to mean a detection in which the dialkyl disulphide component adsorbed on the electrode surface is converted either completely or at least virtually completely to oxidized species such as $R^1$—$SO_2$—$SO_2$—$R^1$ where $R^1$ is an alkyl residue.

For carrying out pulsed amperometric detection, all known different types of carbon and noble metal electrodes are suitable in principle. For reductive determinations, noble metal electrodes, for example gold, silver and gold amalgam electrodes are typically used, and also mercury film electrodes (see J. Frank, Chimia 1981, 35, 24, P. T. Kissinger, C. S. Brunett, K. Bratin, J. R. Rice, Spec. Publ. (U.S.) 1979, 519, 705 and S. Yao, A. Meyer, G. Henze, Fresenius J. Anal. Chem. 1991, 339, 207).

In the context of the method according to the present invention, however, glassy carbon electrodes have proven to be suitable not only for the determination of dialkyl disulphides, but rather as the only working electrode type which allows a reliable determination of dialkyl disulphides. This is indeed surprising since, according to conventional opinion in the literature, carbon electrodes such as glassy carbon electrodes show absolutely no signal for disulphides in the determination of disulphides and thiols, but only for thiols (see C. Terashima et al., Analytical Chemistry, Vol. 75 No. 7, Apr. 1, 2003, 1564-1572). Glassy carbon electrodes typically consist of carbon in the form of pins or small rods having a diameter of 2 to 8 mm, which are cemented or compressed into a glass or plastic holder. In comparison to other carbon electrodes such as carbon paste electrodes, glassy carbon electrodes additionally have an improved chemical resistance, since they are stable in solvents such as methanol or acetonitrile. If required, glassy carbon electrodes can be prepared for use by polishing with a diamond paste, followed by a bath in an ultrasonic bath with high purity water. A further advantage of glassy carbon electrodes is that they allow measurements over a wide range from approx. −0.8V to approx. 1.2V. In the context of the present invention, it has been shown that, in this broad potential range, the electroactive dialkyl disulphides are oxidized completely or at least virtually completely to non-electroactive species. With the aid of glassy carbon electrodes, therefore, the pulsed amperometric detection in oxidative mode can be carried out.

In one embodiment of the method according to the invention, therefore, a glassy carbon electrode is used as working electrode in the pulsed amperometric detection.

With regard to the reference electrode, no limits apply to the method according to the present invention. Therefore, the combination of a glassy carbon electrode with all available electrodes of the first type or the second type is feasible. In the context of the present invention and corresponding to the general expertise of those skilled in the art, electrodes of the first type are understood to mean any electrodes whose potential depends directly on the concentration of the surrounding electrolyte solution. These are solid electrodes such as palladium electrodes. In the context of the present invention and corresponding to the general expertise of those skilled in the art, electrodes of the second type are understood to mean those electrodes whose potential depends only indirectly on the concentration of the surrounding electrolyte solution. The potential of the electrode is constantly maintained by the particular composition of the electrolyte solution. The electrolyte solution consists firstly of a saturated solution of a sparingly soluble salt of which the cation consists of the same metal as the electrode and secondly consists of a readily soluble alkali metal salt of a specific concentration comprising the same anion as the sparingly soluble salt. The potential depends on the concentration of the cation of the sparingly soluble salt. This concentration is in turn coupled with the concentration of the anion via the solubility product. If the concentration of the anion is kept constantly, the potential also therefore remains constant. These anion concentrations can be kept virtually constant by selecting a very large value thereof. The actual potential is given by subtraction of this voltage value from the measured value. Important reference electrodes of the second type are the silver-silver chloride electrode and the calomel electrode. Due to their reliability and problem-free use, the silver-silver chloride reference electrode and palladium reference electrode have proven to be particularly advantageous for the method according to the present invention.

In a further embodiment of the method according to the invention, therefore, a silver-silver chloride electrode or palladium electrode is used as reference electrode in the pulsed amperometric detection.

In principle, three variants for carrying out a pulsed amperometric detection are feasible.

In the first variant, the electrode potential is pulsed over a range in which the analyte is electroactive. The course over time of the applied potential is therefore similar to a step or Heaviside function, wherein however the graph of the potential curve proceeds steadily, and therefore has no interruptions, in contrast to the step function. The course over time of the measurement signal is characterized by a dramatic increase to a maximum value for the electrolysis current and subsequently an immediate decrease of the measured current, which is due to the formation of a diffusion layer around the electrode and the continuous growth of this diffusion layer.

In the second variant, the electrode potential is briefly pulsed over a range in which the analyte is electroactive. In this case, the course over time of the potential applied to the working electrode is characterized in that the starting potential is overlaid at periodic intervals for the same duration by identical rectangular potential blocks. The diffusion layer formed at the working electrode between the pulses can be removed by forced or natural convection. The course over time of the electrolysis current measured is characterized by a dramatic increase and decrease of the electrolysis current which is associated in a timewise manner with the respective pulses. Due to the time limit of the higher electrode potential, the decrease of the measured electrolysis current is limited to the duration of the pulse and accordingly therefore drops lower than in the first variant.

The third variant comprises in total three potential profiles: a first potential profile for conditioning the electrode, a second for sorption of the analytes and finally a third potential profile for the electrooxidation of the analytes in question. The electrolysis current is measured only in relation to the third potential profile.

It has been shown in the context of the present invention that a pulsed amperometric detection with at least three different potential profiles during a complete measurement cycle allows a particularly good reproducibility and reliability of the measurement.

In one embodiment of the method according to the invention, the pulsed amperometric detection therefore includes at least three potential profiles.

The lowest potential profile (or the most electronegative potential profile) preferably serves for the sorption of the analytes at the working electrode and therefore for the conditioning of the working electrode. The highest potential profile (or the most electropositive potential profile) preferably serves for the complete oxidation of adsorbates at the working electrode and therefore effects cleaning of the working electrode. A further potential profile, of which the height lies between the lowest and the highest potential profile, serves for the electrooxidation of the dialkyl disulphide to be determined, and therefore also serves for the measurement of the electrolysis current in question and for determining the dialkyl disulphide concerned.

In the context of the present invention, the sequence of electrooxidation at an oxidation potential, complete oxidation at a cleaning potential and sorption of the analyte at a conditioning potential preferably forms a pulse for a pulsed amperometric detection. Advantageously, a cleaning potential follows an oxidation potential. This has the advantage that the compounds or, if applicable, impurities or residues incompletely oxidized to non-electroactive species during the electrooxidation at the working electrode are completely removed from the working electrode by the application of a cleaning potential electropositive compared to the oxidation potential and the following measurement(s) are therefore not impaired. A conditioning potential preferably follows the cleaning potential. The application of a conditioning potential facilitates the sorption of the analytes to be determined on to the electrode surface. This in turn increases the measurement precision of the subsequent measurement of the electrolysis current during the period in which an oxidation potential is applied to the working electrode. With regard to the number of individual specific potential profiles which may be used in a pulsed amperometric detection, there are no limits in the method according to the invention.

In a preferred embodiment of the method according to the invention, the pulsed amperometric detection therefore includes at least one oxidation potential, at least one cleaning potential and at least one conditioning potential.

Depending on the dialkyl disulphide to be determined, a person skilled in the art can adjust the specific value for the individual potential profile such that, during the time in which the respective potential profiles oxidation potential, cleaning potential and conditioning potential are applied to the working electrode, only the effects assigned to the individual potential profile occur.

It has been shown in the context of the present invention that an electrooxidation at an oxidation potential in the range of approx. +0.5V to approx. +1.3V is suitable for determining all conventional dialkyl disulphides, and in particular for determining dimethyl disulphide, which is an intermediate in the production of commercially important methanesulphonic acid. It has been further shown that a cleaning potential in the range of at least approx. +1.3V is sufficient to ensure complete cleaning of the working electrode of adsorbates or remaining contaminants. For conditioning the working electrode, a conditioning potential in the range of approx. −0.5V to +0.5V has also proven to be suitable in order to facilitate the sorption of the analyte for the subsequent electrooxidation. In the context of the present invention, the term approx. in connection with the data for potential values refers to a deviation of +/−10% from the value explicitly stated.

In a further preferred embodiment of the method according to the invention, the oxidation potential therefore has a value of approx. +0.5V to approx. +1.3V, the cleaning potential has a value of at least approx. +1.3V and the conditioning potential has a value of approx. −0.5V to approx. +0.5V.

For the determination of dialkyl disulphides in alkanesulphonic acids, particularly for the determination of dimethyl disulphide in methanesulphonic acid, an oxidation potential at a value of approx. +0.8V to approx. 1.2V, a cleaning potential at a value of at least approx. +1.5V and a conditioning potential at a value of approx. −0.3V to approx. +0.3V have proven to be particularly suitable to ensure precise and reproducible results.

In a particularly preferred embodiment of the method according to the invention, the oxidation potential therefore has a value of approx. +0.8V to approx. +1.2V, the cleaning potential has a value of at least approx. +1.5V and the conditioning potential has a value of approx. −0.3V to approx. +0.3V.

The application of this and aforementioned potential profiles to the working electrode is not subject to any limits. For example, a specific potential having a constant value from the abovementioned ranges for the potential concerned can be applied to the working electrode during the whole period. A ramp profile for the potential in question is also feasible: In this case, the potential in question at its lowest value from the abovementioned range for this profile is applied to the working electrode at the beginning of the period and the value for the potential is increased to the maximum value from the abovementioned range at a constant potential increase per defined unit of time up to the end of the period.

In order to ensure that the purpose sought by applying the respective potential profile to the working electrode actually occurs, the potential in question has to be applied for a sufficient time to the working electrode. Independent of the dialkyl disulphide to be determined, the following time periods have proven to be convenient with which the effect assigned to the potential profiles oxidation potential, cleaning potential and conditioning potential can also occur: at least approx. 60 ms for the oxidation potential, at least approx. 10 ms for the cleaning potential and at least approx. 40 ms for the conditioning potential. In the context of the present invention, the term approx. in connection with the data for time intervals refers to a deviation of +/−10% from the value explicitly stated. Deviations of this order of magnitude generally do not lead to a notable deterioration of the signal-to-noise ratio.

In a further embodiment of the present invention, the duration of the oxidation potential is at least approx. 60 ms, the duration of the cleaning potential is at least approx. 10 ms and the duration of the conditioning potential is at least approx. 40 ms.

Even if during the time period in which the oxidation potential is applied to the working electrode, in priniciple the corresponding electrolysis current for the respective dialkyl disulphide flows, it is not however measured during the whole time period of the electrolysis current. For at the beginning of the duration of the oxidation potential the electrolysis current is not yet constant. In order to avoid measurement inaccuracies resulting from fluctuations of the electrolysis current, the electrolysis current is therefore first measured after this has adjusted to a constant value. The electrolysis current is typically first measured in the latter half of the duration of the oxidation potential, preferably not until the last third of the duration of the oxidation potential.

The electrolysis current as such constitutes a short-term signal for which, as far as possible, precise measurement of the signal-to-noise ratio is relevant. For measurements of brief amperometric signals, the signal-to-noise ratio is influenced by the instrumental procedure used for the sampling of the electrode current. A significant noise component of the amperometric determination at constant electrode potential, i.e. without pulsing the working electrode potential, is sinusoidal and correlates with the 60 Hz line-change frequency. In order to achieve measurements as far as possible with the aid of pulsed amperometric detection, a signal is therefore used in the context of the present invention that corresponds to the mean of a multiple of the periods of an individual 60 Hz oscillation, i.e. an oscillation period of 16.7 ms. In this case, there is therefore no contribution of the sinusoidal 60 Hz noise signal to the signal strength. The time integral of a sinusoidal 60 Hz noise signal is 0 for every integer multiple v of the periods having an oscillation period of 16.7 ms. The analytical signal strength can therefore be considerably increased for multiples v of the oscillation period which are significantly greater than 1. Therefore, if the analytical signal during the entire period of v*16.7 ms has a constant value, then the signal-to-noise ratio is enhanced by the factor v. In the context of the present invention, integer multiples v of the oscillation period of 16.7 ms of at least 6 have proven to be favourable in order to ensure precise and reproducible results for the electrolysis currents measured in the latter half, preferably in the last third, of the duration of the oxidation potential.

In one embodiment of the method according to the invention, therefore, the measurement duration is an integer multiple of 16.7 ms.

At a duration of at least 300 ms for the oxidation potential, the measurement duration of the electrolysis current is between approx. 100 ms and 150 ms. The measurement period is then preferably approx. 50 ms, approx. 67 ms, approx. 84 ms, approx. 100 ms, approx. 117 ms, approx. 134 ms and approx. 150 ms. In these cases, these are 3-fold, 4-fold, 5-fold, 6-fold, 7-fold, 8-fold or 9-fold of the oscillation period of 16.7 ms.

In a preferred embodiment of the method according to the invention, therefore, the duration of the oxidation potential is at least approx. 300 ms.

At a duration of the oxidation potential of at least approx. 300 ms, the duration of the cleaning potential is then preferably at least approx. 50 ms and the duration of the conditioning potential preferably at least approx. 200 ms.

A typical duration of a measurement cycle composed of oxidation potential, cleaning potential and conditioning potential therefore has a total duration of at least approx. 500 ms.

Since the electrolysis current is typically measured only in the latter half of the duration of the oxidation potential, preferably only in the last third of the duration of the oxidation potential, it is preferably an integer multiple of 16.7 ms and is between one half and one third of the duration of the oxidation potential.

For the chromatographic separation of the analyte comprising the at least one dialkyl disulphide and the alkanesulphonic acid, reversed-phase chromatography has been found to be suitable as chromatographic method in the context of the present invention. The term reversed phase is used in the context of the present invention in relation to the general expertise of those skilled in the art and refers to a non-polar stationary phase such as surface-modified silica gel, which has been rendered non-polar by hydrophobizing the surface thereof with $C_8$-$C_{18}$-alkyl groups, usually $C_8$-alkyl or $C_{18}$-alkyl groups. Polar solvents such as water, methanol or acetonitrile or mixtures thereof are used as mobile phase in the reversed-phase chromatography. The retention times of the analytes are defined by the hydrophobic interactions between the respective analyte and the stationary phase, and also the polarity of the mobile phase. Less polar substances are therefore eluted slowly from a reversed-phase chromatography column, while more polar substances are eluted rapidly from a reversed-phase chromatography column.

This is particularly relevant for the chromatographic separation of samples from the preparation of alkanesulphonic acids by oxidation of dialkyl disulphides. This is because this oxidation proceeds via the formation of S-alkyl alkanethiosulphonates, also referred to as dialkyl thiosulphonates, which, owing to the free electron pair on the sulphur atom of the alkylthioether, the same as on the dialkyl disulphide to be determined, can be absorbed on the working electrode and electrochemically oxidized there. In this case, the S-alkyl alkanethiosulphonates would however influence the measurement of the electrolysis current for the dialkyl disulphide and would lead to higher values for the dialkyl disulphide to be determined. With the aid of reversed-phase chromatography, the dialkyl disulphides can be fully separated from compounds containing sulphur, which can disrupt the determination of the dialkyl disulphides, which guarantees reproducibility and reliability in the values obtained with the method according to the present invention.

In an embodiment of the method according to the invention, therefore, the chromatographic separation is performed by reversed phase chromatography.

With regard to the configuration of carrying out this reversed-phase chromatography, the method according to the present invention is, in principle, not subject to any limitations. Therefore, all feasible configurations of the reversed-phase chromatography, such as ion chromatography or high performance liquid chromatography, can in principle be used in the method according to the present invention. It has been shown, however, that ion chromatography allows a complete separation of the analytes into their individual constituents at reasonable cost and effort. Moreover, ion chromatography has the advantage, compared to high-performance chromatography, that it allows a greater number of possibilities for adjusting the parameters for (as far as possible) optimal separating conditions.

In a preferred embodiment of the method according to the invention, therefore, the chromatographic separation is performed by ion chromatography.

Suitable polar solvents for carrying out the reversed-phase chromatography for dialkyl disulphides in alkanesulphonic acids have been shown to be protic solvents such as methanol, ethanol and water. In the context of the present invention, the term protic solvent is used in line with the general expertise of those skilled in the art and therefore refers to such compounds having a functional group in the molecule from which hydrogen atoms can be cleaved as protons.

In a further embodiment of the method according to the invention, therefore, the method according to the invention additionally comprises the step of providing an analyte, preceding the determination of the dimethyl disulphide, by dissolving a sample comprising the dimethyl disulphide and methanesulphonic acid in a protic solvent or a mixture of protic solvents.

In the context of the present invention, a mixture of methanol and water has proven to be particularly suitable for carrying out the chromatographic separation.

A mixture of methanol and water for the dissolution of the sample containing a dialkyl disulphide and an alkanesulphonic acid is therefore preferably used in the method according to the invention.

The eluent for the chromatographic separation preferably comprises methanol and water in a ratio by volume of 3:7.

By dissolving the sample containing the dialkyl disulphide and the alkane sulphonic acid in a protic solvent or a mixture of protic solvents, this sample is diluted.

By providing an analyte in which a sample containing a dialkyl disulphide and an alkane sulphonic acid is preferably dissolved in a protic solvent or a mixture of protic solvents, this sample is diluted by a factor of approx. 10 to approx. 1000.

The eluent used for the chromatographic separation flows through the amperometric measuring cell after exit from the chromatography column. Therefore, the protic solvent or the mixture of protic solvents used for the dissolution of the sample must fulfil not only the function of an eluent in the chromatographic separation but also that of an electrolyte in the subsequent determination of the dialkyl disulphide by means of pulsed amperometric detection. This presupposes an intrinsic conductivity of the solvent or solvent mixture in question, which is generally not achieved alone by ions such as chloride, nitrate or the like additionally present in the sample. In the simplest case, the required conductivity is supplied by the alkanesulphonic acid, preferably methanesulphonic acid, present in the sample.

The method according to the present invention and the advantages thereof are further elucidated by the following examples and comparative examples.

FIGURES

FIG. 1: Chromatogram of comparative example 1
FIG. 2: Chromatogram of comparative example 2
FIG. 3: Chromatogram of comparative example 3
FIG. 4: Chromatogram of comparative example 4
FIG. 5: Chromatogram of example 1
FIG. 6: Chromatogram of example 2
FIG. 7: Chromatogram of example 3
FIG. 8: Chromatogram of example 4
FIG. 9: $^1$H-NMR spectrum of comparative experiment 5

EXAMPLES

I. Technical Equipment

1. Equipment Used:

Professional Sample Processor 858 (No. 2.858.0010 from Metrohm) sample handling device equipped with an 800 Dosino 800 (No. 2.800.0010 from Metrohm) metering system.

882 Compact IC plus (No. 2.850.9110 from Metrohm) ion chromatograph equipped with a Vario 944 (No. 2.944.0010 from Metrohm) UV/VIS detector, an IC Amperometric Detector (No. 2.850.9110 from Metrohm) and a pressure gauge.

883 Basic IC plus (2.883.0020 from Metrohm) ion chromatograph equipped with a conductitvity detector in the form of the module iDetector (standard equipment of the 883 Basic IC plus ion chromtograph) and a pressure gauge.

In the experiments, the first device is the sample handling system, followed by the ion chromatograph which is equipped with a relevant detector.

2. Chromatographic Columns:

In the 882 Compact IC plus ion chromatograph, a column of the type Phenomenex® Gemini® 5U C6-Phenyl 110A 250/4.6 is used. Alternatively, a column of the type ProntoSil 120-5-C18 AQ 150/4.0 (6.1008.100 from Metrohm) may also be used.

In the 883 Basic IC Plus ion chromatograph, a Metrosep A Supp 1 Guard/4.6 is used as pre-column or guard column and an anion separating column Metrosep A Supp 5 250/4.0 is used as main column. A Metrohm Suppressor-Module MSM is also used as cation exchanger.

3. Eluents:

Chemicals Used:
ultrapure water having a conductivity resistance of 18.2 MOhm and a TOC of 5 ppb, where TOC represents total organic carbon and gives the sum total of the organic carbon in a water sample (from a Milli-Q Advantage A10 ultrapure water system with Q-POC dispenser or a Millipore system),
LiChrosolv HPLC Grade (high performance liquid chromatography) methanol (1.06007 from Merck),
Potassium dihydrogen phosphate 99% (1.04873 from Merck),
Phosphoric acid 85% (1.00573 from Merck), and
Methanesulphonic acid (471356 from Sigma Aldrich).

The eluent for the 882 Compact IC plus ion chromatograph is composed of:
70% ultrapure water,
30% methanol,
10% potassium dihydrogen phosphate, and
1.2 g phosphoric acid.

The eluent for the 883 Basic IC plus ion chromatograph is composed of:
100% ultrapure water,
3.2 mmol of sodium carbonate, and
1.0 mmol of dihydrogen carbonate.

II. Amperometric Detection at Constant Voltage

For comparison with pulsed amperometric detection, dimethyl disulphide (DMDS) in a sample from the preparation of methanesulphonic acid (MSA) by oxidation of dimethyl disulphide was determined by means of amperometric detection at constant voltage.

An analyte was used for this purpose (referred to as analyte V below), which was provided by dissolving 2 drops of the sample from the methanesulphonic acid preparation in 50 mL of a mixture of acetonitrile and water (ratio by volume 30:70). The measurements were carried out over a period of about one hour using a 882 Compact IC Plus 1 ion chromatograph (2.850.9110 from Metrohm), which is equipped with a ProntoSil 120-5-C18 AQ-150/4.0 separating column (6.1008.100 from Metrohm), a Metrosep RP2 Guard/3.5 (6.1011.030 from Metrohm) and an amperometric detector (2.850.9110 from Metrohm). This detector has a measurement cell of the wall jet cell type (6.5337.020 from Metrohm), which is equipped with a glassy carbon working electrode (6.1257.220 from Metrohm) of 3 mm diameter, a silver/silver chloride reference electrode (6.1257.720 from Metrohm) and an auxiliary electrode (6.1247.000 from Metrohm). The injection volume was 20 µl and the temperature of the separating column was held at approx. 25° C.

The determinations of dimethyl disulphide were then compared with one another in order to be able to evaluate the reproducibility and reliability of the amperometric determination at constant voltage. For this purpose, the values for the area under the peak for dimethyl disulphide in the relevant chromatograms were compared with one another.

Comparative Example 1

At the time point t=0, the analyte V was injected into the ion chromatograph. The parameters for the ion chromatography carried out are:
Eluent: MeOH:H$_2$O (3:7)+2 g/l KH$_2$PO$_4$+2 g/l H$_3$PO$_4$
Flow rate: 1.2 ml/min
Pressure: 173.1 bar
Recording duration: 20.7 min The components determined in the eluate of this ion chromatography are listed in table 1 and the chromatogram of this determination is shown in FIG. 1. The number of the peaks in this table agrees with the correspondingly numbered peaks in the chromatogram of FIG. 1.

TABLE 1

Results of the determination in comparative example 1

| Peak No. | Retention time [min] | Area (nA) * min | Height [nA] | Component |
|---|---|---|---|---|
| 1 | 2.997 | 0.0253 | 0.176 | Bromide |
| 2 | 3.457 | 0.0163 | 0.148 | Nitrate |
| 3 | 4.415 | 0.4227 | 3.483 | Phosphate |
| 4 | 15.835 | 352.7363 | 958.275 | DMDS |

Comparative Example 2

At the time point t=22 min, the analyte V was injected into the ion chromatograph. The parameters for the ion chromatography carried out are:
Eluent: MeOH:$H_2O$ (3:7)+2 g/l $KH_2PO_4$+2 g/l $H_3PO_4$
Flow rate: 1.2 ml/min
Pressure: 170.8 bar
Recording duration: 18.5 min The components determined in the eluate of this ion chromatography are listed in table 2 and the chromatogram of this determination is shown in FIG. 2. The number of the peaks in this table agrees with the correspondingly numbered peaks in the chromatogram of FIG. 2.

TABLE 2

Results of the determination in comparative example 2

| Peak No. | Retention time [min] | Area (nA) * min | Height [nA] | Component |
|---|---|---|---|---|
| 1 | 2.988 | 0.0230 | 0.163 | Bromide |
| 2 | 3.455 | 0.0140 | 0.149 | Nitrate |
| 3 | 4.405 | 0.3272 | 2.717 | Phosphate |
| 4 | 15.752 | 321.3513 | 891.404 | DMDS |

In identical analytes using amperometric determination at constant voltage, 22 minutes after the first measurement already an approximately 8.9% lower area value is obtained for the determination of dimethyl disulphide in methanesulphonic acid.

Comparative Example 3

At the time point t=42 min, the analyte V was injected into the ion chromatograph. The parameters for the ion chromatography carried out are:
Eluent: MeOH:$H_2O$ (3:7)+2 g/l $KH_2PO_4$+2 g/l $H_3PO_4$
Flow rate: 1.2 ml/min
Pressure: 173.1 bar
Recording duration: 20.7 min The components determined in the eluate of this ion chromatography are listed in table 3 and the chromatogram of this determination is shown in FIG. 3. The number of the peaks in this table agrees with the correspondingly numbered peaks in the chromatogram of FIG. 3.

TABLE 3

Results of the determination in comparative example 3

| Peak No. | Retention time [min] | Area (nA) * min | Height [nA] | Component |
|---|---|---|---|---|
| 1 | 1.908 | 0.0337 | 0.175 | MSA |
| 2 | 2.992 | 0.0234 | 0.175 | Bromide |
| 3 | 3.458 | 0.0148 | 0.154 | Nitrate |

TABLE 3-continued

Results of the determination in comparative example 3

| Peak No. | Retention time [min] | Area (nA) * min | Height [nA] | Component |
|---|---|---|---|---|
| 4 | 4.403 | 0.2953 | 2.442 | Phosphate |
| 5 | 6.002 | 0.0066 | 0.030 | MMTS |
| 6 | 15.705 | 303.7108 | 853.682 | DMDS |

By means of amperometric determination at constant voltage, already 42 minutes after the first measurement an approximately 13.9% lower area value is obtained for dimethyl disulphide.

Comparative Example 4

At the time point t=62 min, the analyte V was injected into the ion chromatograph. The parameters for the ion chromatography carried out are:
Eluent: MeOH:$H_2O$ (3:7)+2 g/l $KH_2PO_4$+2 g/l $H_3PO_4$
Flow rate: 1.2 ml/min
Pressure: 168.0 bar
Recording duration: 25.0 min The components determined in the eluate of this ion chromatography are listed in table 4 and the chromatogram of this determination is shown in FIG. 4. The number of the peaks in this table agrees with the correspondingly numbered peaks in the chromatogram of FIG. 4.

TABLE 4

Results of the determination in comparative example 4

| Peak No. | Retention time [min] | Area (nA) * min | Height [nA] | Component |
|---|---|---|---|---|
| 1 | 2.720 | 0.0037 | 0.059 | Nitrite |
| 2 | 3.000 | 0.0232 | 0.150 | Bromide |
| 3 | 3.468 | 0.0191 | 0.154 | Nitrate |
| 4 | 4.402 | 0.2589 | 2.106 | Phosphate |
| 5 | 15.682 | 275.3675 | 771.120 | DMDS |

62 minutes after the first measurement, the area value for the determination of dimethyl disulphide is actually about 21.9% below the starting value.

Comparative experiments 1 to 4 show that amperometric detection at constant voltage is basically unsuitable for reproducible and reliable determination of dialkyl disulphides in alkanesulphonic acids and particularly of dimethyl disulphides in methanesulphonic acid.

III. Pulsed Amperometric Detection

By means of pulsed amperometric detection, dimethyl disulphide in a sample from the preparation of methanesulphonic acid by oxidation of dimethyl disulphide was determined over a period of more than one hour.

An analyte was used for this purpose (referred to as analyte B below), which was provided by dissolving 3 drops of the sample from the methanesulphonic acid preparation in 100 mL of a mixture of acetonitrile and water (ratio by volume 30:70).

The same instrumental arrangement was used as for the amperometric detection at constant voltage. The injection volume was 20 µl and the temperature of the separating column was held at approx. 25° C.

The electrooxidation potential has a value of 1.15V and a duration of 300 ms, wherein the measurement duration is 100 ms. The cleaning potential has a value of 1.5V and lasts 50 ms and the conditioning potential has a value of 0.1V and a duration of 200 ms. The total duration of a measurement cycle is therefore 550 ms.

Example 1

At the time point t=0 min, the analyte B was injected into the ion chromatograph. The parameters for the ion chromatography carried out are:
Eluent: MeOH:$H_2O$ (3:7)+4.2 g/l $KH_2PO_{4+}$0.2 g/l $H_3PO_4$
Flow rate: 1.2 ml/min
Pressure: 160.1 bar
Recording duration: 25.0 min The components determined in the eluate of this ion chromatography are listed in table 5 and the chromatogram of this determination is shown in FIG. 5. The number of the peaks in this table agrees with the correspondingly numbered peaks in the chromatogram of FIG. 5.

TABLE 5

Results of the determination in example 1

| Peak No. | Retention time [min] | Area (nA) * min | Height [nA] | Component |
| --- | --- | --- | --- | --- |
| 1 | 1.631 | 3.7303 | 17.486 | Fluoride |
| 2 | 4.390 | 5.6792 | 48.794 | Phosphate |
| 3 | 6.644 | 0.2156 | 1.330 | MMTS |
| 4 | 15.716 | 333.7089 | 771.120 | DMDS |

Example 2

At the time point t=42 min, the analyte B was injected into the ion chromatograph. The parameters for the ion chromatography carried out are:
Eluent: MeOH:$H_2O$ (3:7)+4.2 g/l $KH_2PO_{4+}$0.2 g/l $H_3PO_4$
Flow rate: 1.2 ml/min
Pressure: 161.2 bar
Recording duration: 21.7 min The components determined in the eluate of this ion chromatography are listed in table 6 and the chromatogram of this determination is shown in FIG. 6. The number of the peaks in this table agrees with the correspondingly numbered peaks in the chromatogram of FIG. 6.

TABLE 6

Results of the determination in example 2

| Peak No. | Retention time [min] | Area (nA) * min | Height [nA] | Component |
| --- | --- | --- | --- | --- |
| 1 | 3.620 | 0.7375 | 6.608 | Nitrate |
| 2 | 4.985 | 0.2138 | 1.922 | Phosphate |
| 3 | 15.689 | 327.0947 | 825.014 | DMDS |

Example 3

At the time point t=2.5 h, the analyte B was injected into the ion chromatograph. The parameters for the ion chromatography carried out are:
Eluent: MeOH:$H_2O$ (3:7)+4.2 g/l $KH_2PO_{4+}$0.2 g/l $H_3PO_4$
Flow rate: 1.2 ml/min
Pressure: 161.2 bar
Recording duration: 21.7 min The components determined in the eluate of this ion chromatography are listed in table 7 and the chromatogram of this determination is shown in FIG. 7. The number of the peaks in this table agrees with the correspondingly numbered peaks in the chromatogram of FIG. 7.

TABLE 7

Results of the determination in example 3

| Peak No. | Retention time [min] | Area (nA) * min | Height [nA] | Component |
| --- | --- | --- | --- | --- |
| 1 | 1.576 | 0.4106 | 8.942 | Fluoride |
| 2 | 3.629 | 0.4906 | 4.236 | Nitrate |
| 3 | 4.994 | 0.2911 | 1.955 | Phosphate |
| 4 | 15.652 | 332.5320 | 811.847 | DMDS |

Discussion of the Measurement Results:

To evaluate the precision of the pulsed amperometric detection, the values for the area under the peaks for dimethyl disulphide determined in examples 1 to 3 are used. This value is then a reference point for the concentration of the dimethyl disulphide to be determined.

The area values determined in examples 1 and 2 only deviate from each other by about 1.98%. The deviation of the area values determined in examples 1 and 3, the furthest from each other in terms of time, is actually only 0.35%. Since the values determined in examples 1 and 3 are virtually identical, the pulsed amperometric detection therefore allows reliable determination of dimethyl disulphide. The deviation apparent in example 2 is not therefore due to a possible lack of reproducibility of the measurement results but due to a measurement error.

The dimethyl disulphide concentration determined in this example is identical with that from example 1. Moreover, the deviation from the area value determined in example 1 is only 0.35%, which is still significantly below the already low measurement error of example 2.

Compared to comparative examples 2 to 4, the deviations of the area value in examples 2 and 3 are considerably lower and this also over a period which is more than double as long as the total measurement duration in the comparative examples. Consequently, pulsed amperometric detection represents a reliable and reproducible determination of dimethyl disulphide in methanesulphonic acid.

IV. Comparison of Ion Chromatography and Pulsed Amperomertry with NMR

After it has been shown that pulsed amperometric detection is a suitable method for the reproducible and reliable determination of dialkyl disulphides in alkanesulphonic acids, particularly of dimethyl disulphide in methanesulphonic acid, the precision of this method was compared with nuclear magnetic resonance.

Example 4

The same instrumental arrangement was used as for the amperometric detection at constant voltage.

A mixture of 3 drops of a sample from the preparation of methanesulphonic acid by oxidation of dimethyl disulphide in 100 mL of a mixture of acetonitrile and water (30:70 v/v) was used as analyte. The injection volume was 20 µl and the temperature of the separating column was held at approx. 25° C.
Eluent: MeOH:$H_2O$ (3:7)+4.2 g/l $KH_2PO_{4+}$0.2 g/l $H_3PO_4$
Flow rate: 1.2 ml/min
Pressure: 162.3 bar
Recording duration: 25.0 min The components determined in the eluate of this ion chromatography are listed in table 8 and the chromatogram of this determination is shown in FIG. 8. The number of the peaks in this table agrees with the correspondingly numbered peaks in the chromatogram of FIG. 8.

TABLE 8

Results of the determination in example 5

| Peak No. | Retention time [min] | Area (nA) * min | Height [nA] | Concentration [wt %] | Component |
|---|---|---|---|---|---|
| 1 | 1.686 | 2.3189 | 8.449 | — | MSA |
| 2 | 3.510 | 2.5620 | 12.960 | — | Nitrate |
| 3 | 15.926 | 190.6092 | 430.759 | 2.567 | DMDS |

Comparative Example 5

Dimethyl disulphide in methanesulphonic acid was also determined by means of nuclear magnetic resonance. The analyte used for this determination is composed of 26.95 mg of a sample from the preparation of methanesulphonic acid by oxidation of dimethyl disulphide and 39.16 mg of naphthalene, wherein the compound last mentioned serves as solvent due to its inert character with respect to dimethyl disulphide and methanesulphonic acid. The nuclear magnetic resonance measurement was carried out using a 600 MHz Bruker Avance (III) spectrometer from Bruker Niospin, equipped with a Bruker Ascend 600 MHz magnet system from Bruker Biospin and a Prodigy CryoProbe probe head and also using MeOD as deuterated solvent. The measurement time was 20 minutes.

The proton spectrum of this measurement is shown in FIG. 9, and the results obtained from this spectrum are summarized in table 9.

Nuclear magnetic resonance allows the determination of dimethyl disulphide with a precision of one decimal place or 0.1% by weight, while pulsed amperometric detection enables a determination of dimethyl disulphide up to 3 decimal places or 0.001% by weight, which represents a greater precision by a factor of 100.

The dimethyl disulphide concentration determined in examples 1 to 5 and in comparative example 5 always refers to the concentration of this component in the respective analyte. Since this analyte, however, represents a dilution of the sample from the methanesulphonic acid preparation, the actual concentration of the dimethyl disulphide in this sample is higher by this dilution factor. Consequently, the differences between NMR analysis and pulsed amperometric detection are more notable in more concentrated samples. By reason of its detection limit, about a factor 100 better compared to NMR analysis, pulsed amperometric detection is therefore the method of choice for determining a dialkyl disulphide in an alkanesulphonic acid.

V. Comparison of the Pulsed Amperometric Detector with a UV Detector

The higher sensitivity of the (pulsed) amperometric detector for a dialkyl disulphide in an alkanesulphonic acid was shown by a measurement series with a dilution series of dimethyl disulphide in methanesulphonic acid.

1. Sample Preparation:

The samples are composed of the weighings according to table 10 which were weighed out on a four-figure analytical balance. For calibration in the ppm range, one drop of the sample was weighed onto 100 g of ultrapure water. A liquid sample was placed in a 4 ml volume sample vial (Rotilabor) and then sealed with a screw cap with seal. The sample was then placed in the sample rack of the 858 Professional Sample Processor. The further dilution of the sample was carried out by the sample handler. This is carried out in a mixing vessel with magnetic stirrer, wherein the sample is diluted in a ratio of 1:100. The sample was then pumped into one or more sample loops of different lengths. In a 882 Compact IC plus ion chromatograph, equipped with a column of the type Gemini 5U C6-Phenyl 110A 250/4.6, the sample loop has a length of 20 µl. Cleaning steps for the mixing vessel then followed for the next analysis.

2. Deviations/Errors:

A deviation of approx. 2% is in the limits of the precision ion chromatography. For the determination of dimethyl disulphide, calibrations of the order of magnitude of 50 ppm are possible, and for methyl methanethiosulphonate (MMTS) calibrations of the order of magnitude of 100 ppm are possible. At still lower concentrations, the errors are significantly greater than the acceptable deviation of 2%.

3. Results

An 882 Compact IC plus (No. 2.850.9110 from Metrohm) ion chromatograph was used, equipped with a Vario 944 (No. 2.944.0010 from Metrohm) UV/VIS detector, an IC Amperometric Detector (No. 2.850.9110 from Metrohm) and a pressure gauge, which serves to keep track of a constant pressure during the spectral recording.

4 experiments were carried out with the inputs stated in table 10 for the respective analytes.

TABLE 10

Summary of the analytes and the measurement results

| Experiment | Component | Weight | Nominal value % | Actual value % | Deviation % | Detector |
|---|---|---|---|---|---|---|
| 1 | MSA | 45.77 | 90.05 | 90 | 0.06 | LF |
|   | MMTS | 1.95 | 3.84 | 3.849 | 0.12 | UV 210 |
|   | DMDS | 3.10 | 6.10 | 6.108 | 0.08 | AD |
|   |      |      |      | 6.109 | 0.10 | UV 210 |
| 2 | MSA | 47.56 | 95.00 | 94.33 | −0.07 | LF |
|   | MMTS | 0.99 | 1.98 | 1.941 | −1.75 | UV 210 |
|   | DMDS | 1.52 | 3.03 | 3.011 | −0.57 | AD |
|   |      |      |      | 3.007 | −0.70 | UV 210 |

TABLE 9

Results of the determination in comparative example 5

| Peak No. | Component | Integral | Factor | Corrected integral | Ratio [mol %] | Amount [mmol] | Molar mass [g/mol] | Mass [mg] | Content [wt %] |
|---|---|---|---|---|---|---|---|---|---|
|   | Naphthalene | 464.047 | 4 | 116.012 | 53.0 | 0.305 | 128.16 | 39.07 | — |
| 1 | MSA | 300.000 | 3 | 100.000 | 45.7 | 0.263 | 96.11 | 25.26 | 93.7 |
| 2 | DMDS | 16.952 | 6 | 2.825 | 1.3 | 0.007 | 94.20 | 0.70 | 2.6 |

TABLE 10-continued

Summary of the analytes and the measurement results

| Experiment | Component | Weight | Nominal value % | Actual value % | Deviation % | Detector |
|---|---|---|---|---|---|---|
| 3 | MSA | 49.14 | 97.98 | 97.79 | −0.19 | LF |
|  | MMTS | 0.5179 | 1.0320 | 1.079 | 4.56 | UV 210 |
|  | DMDS | 0.4976 | 0.9921 | 0.996 | 0.40 | AD |
|  |  |  |  | 1 | 0.80 | UV 210 |
| 4 | MSA | 49.66 | 99.28 | 99.40 | 0.13 | LF |
|  | MMTS | 0.1108 | 0.2214 | 0.19 | −14.19 | UV 210 |
|  | DMDS | 0.2519 | 0.5034 | 0.518 | 2.89 | AD |
|  |  |  |  | 0.521 | 3.49 | UV 210 |

The measurement results summarized in table 10 show that a (pulsed) amperometric detector is superior to a UV/VIS spectrometer in terms of the precision in the determination of dimethyl disulphide. This greater precision of amperometry in the determination of dimethyl disulphide increases still further with increasing dilution of the dimethyl disulphide in the methanesulphonic acid.

The invention claimed is:

1. A method for determining dimethyl disulphide, the method comprising:
   a) carrying out a chromatographic separation of an analyte comprising at least dimethyl disulphide and methanesulphonic acid; and
   b) determining the dimethyl disulphide by pulsed amperometric detection,
   wherein a glassy carbon electrode is used as a working electrode in the pulsed amperometric detection.

2. The method according to claim 1, wherein the determining of the dimethyl disulphide by the pulsed amperometric detection further comprises:
   b1) measuring an electrolysis current for the dimethyl disulphide by the pulsed amperometric detection; and
   b2) determining an amount of the dimethyl disulphide, a concentration of the dimethyl disulphide, or both, by comparison with a calibration function previously generated for the dimethyl disulphide.

3. The method according to claim 1, wherein the pulsed amperometric detection is carried out in an oxidative mode.

4. The method according to claim 1, wherein a silver-silver chloride electrode or a palladium electrode is used as a reference electrode in the pulsed amperometric detection.

5. The method according to claim 1, wherein the pulsed amperometric detection includes at least three potential profiles.

6. The method according to claim 5, wherein the pulsed amperometric detection comprises at least one oxidation potential, at least one cleaning potential and at least one conditioning potential.

7. The method according to claim 6, wherein the oxidation potential has a value of approximately +0.5V to approximately +1.3V, the cleaning potential has a value of at least approximately +1.3V, and the conditioning potential has a value of approximately −0.5V to approximately +0.5V.

8. The method according to claim 6, wherein the oxidation potential has a value of approximately +0.8V to approximately +1.2V, the cleaning potential has a value of at least approximately +1.5V, and the conditioning potential has a value of approximately 0.3V to approximately +0.3V.

9. The method according to claim 6, wherein a duration of the oxidation potential is at least approximately 60 ms, a duration of the cleaning potential is at least approximately 10 ms, and a duration of the conditioning potential is at least approximately 40 ms.

10. The method according to claim 9, wherein the duration of the oxidation potential is at least approximately 300 ms.

11. The method according to claim 2, wherein a measurement duration of the pulsed amperometric detection is an integer multiple of 16.7 ms.

12. The method according to claim 1, wherein the chromatographic separation is performed by reversed phase chromatography.

13. The method according to claim 12, wherein the chromatographic separation is performed by ion chromatography.

14. The method according to claim 1, wherein the analyte is provided, by dissolving a sample comprising the dimethyl disulphide and the methanesulphonic acid in a protic solvent or in a mixture of protic solvents.

* * * * *